United States Patent
Penzimer et al.

(10) Patent No.: US 9,282,977 B2
(45) Date of Patent: Mar. 15, 2016

(54) METHODS FOR BONE FIXATION USING AN INTRAMEDULLARY FIXATION IMPLANT

(71) Applicant: Extremity Medical LLC, Parsippany, NJ (US)

(72) Inventors: Raymond Penzimer, Morristown, NJ (US); James Gannoe, West Milford, NJ (US)

(73) Assignee: EXTREMITY MEDICAL LLC, Parsippany, NJ (US)

( * ) Notice: Subject to any disclaimer, the term of this patent is extended or adjusted under 35 U.S.C. 154(b) by 0 days.

(21) Appl. No.: 14/521,913

(22) Filed: Oct. 23, 2014

(65) Prior Publication Data

US 2015/0112342 A1   Apr. 23, 2015

Related U.S. Application Data

(60) Provisional application No. 61/894,564, filed on Oct. 23, 2013.

(51) Int. Cl.
*A61B 17/58* (2006.01)
*A61B 17/72* (2006.01)
*A61B 17/88* (2006.01)
*A61F 2/30* (2006.01)
*A61B 17/16* (2006.01)

(52) U.S. Cl.
CPC ........... *A61B 17/164* (2013.01); *A61B 17/1682* (2013.01); *A61B 17/1686* (2013.01); *A61B 17/7266* (2013.01); *A61B 17/7291* (2013.01); *A61B 17/8875* (2013.01)

(58) Field of Classification Search
CPC ........ A61B 17/68; A61B 17/72; A61B 17/84; A61B 17/844; A61B 17/88; A61B 17/7291; A61B 17/7266; A61B 2017/681; A61F 2/4225–2/4241; A61F 2002/30622; A61F 2002/4243–2002/4258

See application file for complete search history.

(56) References Cited

U.S. PATENT DOCUMENTS 3,115,804 A * 12/1963 Johnson ................ F16B 21/086
                                                           411/338
4,091,806 A   5/1978 Aginsky
4,590,928 A   5/1986 Hunt et al.
(Continued)

FOREIGN PATENT DOCUMENTS

FR        2801189 A1    5/2001
GB        2430625 A     4/2007
WO   WO2006109004      10/2006

OTHER PUBLICATIONS

PCT International Search Report for International Application No. PCT/US14/61948 dated Apr. 28, 2015.

*Primary Examiner* — Jacqueline Johanas
(74) *Attorney, Agent, or Firm* — Kelley Drye & Warren LLP

(57) ABSTRACT

The invention comprises an intramedullary fixation implant and a method for joining bones and translating compression between the bones for treating various digital deformities. The intramedullary fixation implant comprises a first fixation portion and a second fixation portion connected to the first fixation portion, wherein the second fixation portion comprises a first projection and a second projection separated by a slot, and wherein the first projection and the second projection comprise a plurality of barbs shaped and arranged along the first and second projections such that they cooperatively form a thread along the second fixation portion.

20 Claims, 19 Drawing Sheets

(56) References Cited

U.S. PATENT DOCUMENTS

| | | |
|---|---|---|
| 4,955,916 A | 9/1990 | Carignan et al. |
| 5,047,059 A | 9/1991 | Saffar |
| 5,417,692 A | 5/1995 | Goble et al. |
| 5,425,777 A | 6/1995 | Sarkisian et al. |
| 5,601,558 A | 2/1997 | Torrie et al. |
| 5,634,925 A | 6/1997 | Urbanski |
| 5,951,288 A | 9/1999 | Sawa |
| 6,413,260 B1 | 7/2002 | Berrevoets et al. |
| 6,458,134 B1 | 10/2002 | Songer et al. |
| 6,517,543 B1 | 2/2003 | Berrevoets et al. |
| 7,041,106 B1 | 5/2006 | Carver et al. |
| 8,262,712 B2 | 9/2012 | Coilard-Lavirotte et al. |
| 8,394,097 B2 | 3/2013 | Peyrot et al. |
| 8,414,583 B2 | 4/2013 | Prandi et al. |
| 8,475,456 B2 | 7/2013 | Augoyard et al. |
| 2004/0002759 A1 | 1/2004 | Ferree |
| 2008/0177291 A1 | 7/2008 | Jensen et al. |
| 2011/0004255 A1 | 1/2011 | Weiner et al. |
| 2011/0082508 A1 | 4/2011 | Reed |
| 2011/0144644 A1 | 6/2011 | Prandi |
| 2011/0184472 A1 | 7/2011 | Niederberger et al. |
| 2011/0257652 A1 | 10/2011 | Roman |
| 2011/0301652 A1 | 12/2011 | Reed et al. |
| 2011/0301653 A1 | 12/2011 | Reed et al. |
| 2012/0029579 A1 | 2/2012 | Bottlang |
| 2012/0065692 A1 | 3/2012 | Champagne et al. |
| 2012/0089197 A1 | 4/2012 | Anderson |
| 2013/0053975 A1 | 2/2013 | Reed et al. |
| 2013/0060295 A1 | 3/2013 | Reed et al. |
| 2013/0066383 A1 | 3/2013 | Anderson et al. |
| 2013/0123862 A1 | 5/2013 | Anderson et al. |
| 2013/0131822 A1 | 5/2013 | Lewis |
| 2013/0190761 A1 | 7/2013 | Prandi et al. |
| 2013/0226191 A1 | 8/2013 | Thoren et al. |
| 2013/0274814 A1* | 10/2013 | Weiner ............... A61B 17/7291 606/301 |
| 2014/0188179 A1* | 7/2014 | McCormick ....... A61B 17/7291 606/301 |
| 2014/0277186 A1* | 9/2014 | Granberry .......... A61B 17/1682 606/301 |
| 2014/0277554 A1* | 9/2014 | Roman ................. A61F 2/4225 623/21.19 |
| 2015/0011998 A1* | 1/2015 | McCormick ........... A61F 5/019 606/56 |
| 2015/0073413 A1* | 3/2015 | Palmer ............... A61B 17/7266 606/63 |
| 2015/0112341 A1* | 4/2015 | Penzimer ........... A61B 17/8875 606/62 |
| 2015/0112342 A1* | 4/2015 | Penzimer ........... A61B 17/8875 606/63 |
| 2015/0164563 A1* | 6/2015 | Lewis .................. A61F 2/4606 606/63 |
| 2015/0223850 A1* | 8/2015 | Reed .................. A61B 17/7225 606/329 |

* cited by examiner

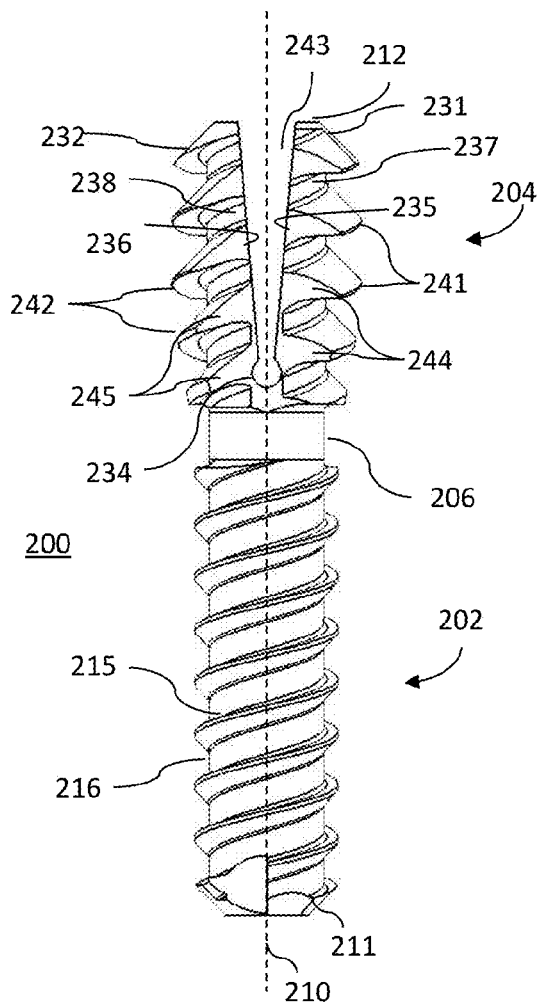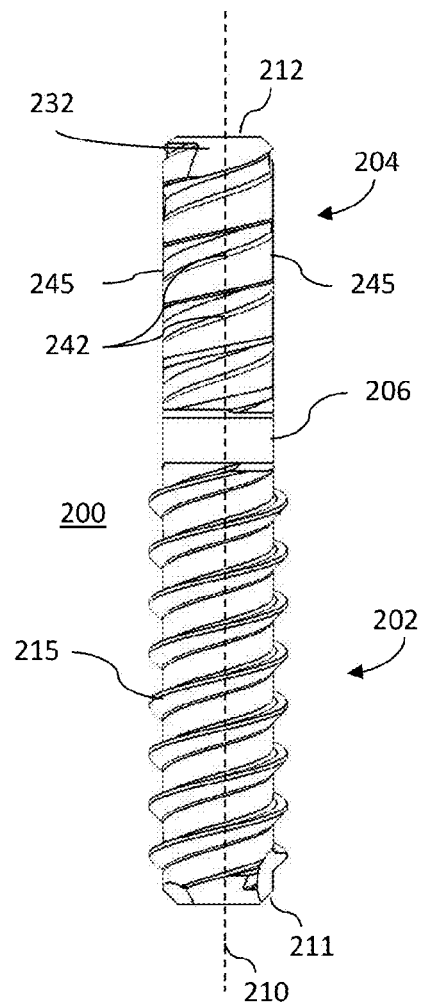
FIG. 3B  FIG. 3C
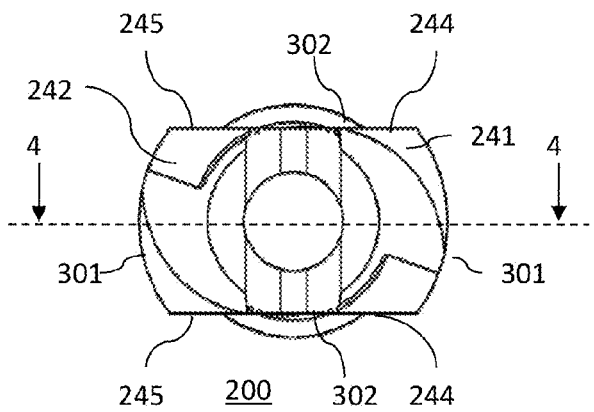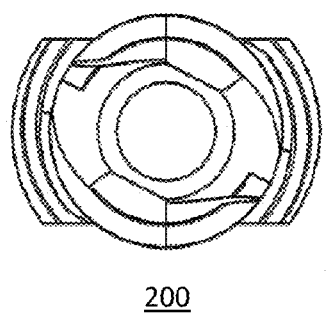
FIG. 3D  FIG. 3E

METHODS FOR BONE FIXATION USING AN INTRAMEDULLARY FIXATION IMPLANT

CROSS-REFERENCE TO RELATED APPLICATIONS

This application claims the benefit of U.S. Provisional Application Ser. No. 61/894,564, filed on Oct. 23, 2013, the entire contents of which are herein incorporated by reference. This application is also related to U.S. application Ser. No. 14/521,879, filed Oct. 23, 2014, entitled "Devices For Bone Fixation Using An Intramedullary Fixation Implant," the entire contents of which are herein incorporated by reference.

FIELD OF THE INVENTION

This invention relates to the field of implant devices for bone fixation, and more particularly, to an intramedullary fixation implant used for the fixation of bones and the correction of deformities in the foot or the hand, such as a hammertoe deformity.

BACKGROUND OF THE INVENTION

Digital deformities are among the most common forefoot pathologies encountered by podiatrists and orthopedic surgeons. Digital deformities may occur in the form of hammertoes, claw toes, mallet toes, bone spurs, overlapping and underlapping toes, mallet fingers, jersey fingers, and coach's fingers, among others. The deformities typically affect the interphalangeal joints of the hand or the foot, metatarsophalangeal joints of the foot, or metacarpophalangeal joint of the hand. Digital deformities in the fingers or toes result from imbalance of the tendons, causing them to stretch or tighten abnormally. These deformities may be either congenital or acquired. For example, the deformities may be cause by neuromuscular and arthritic disorders, systemic diseases, flat or high-arched feet, or traumatic injuries to the joints. Toe deformities can also be aggravated by poorly fitting footwear.

Hammertoe, for example, results in a bend in the middle joint of the toe into a claw-like deformity. While at first the patient may be able to move and straighten the toe, overtime the hammertoe may become fixed. In this contracted position, the inside of the shoe rubs against the contracted joints, causing corns to form on the top of the toe and calluses to form on the sole of the foot. In certain patients these corns and calluses may open or ulcerate and form wounds. This causes pain and discomfort in walking or wearing shoes. FIG. 1A depicts a human foot 100 afflicted with hammertoe deformity. Distal phalanx 101, middle phalanx 103, proximal phalanx 105, and metatarsal 107 bones are depicted in foot 100. The distal interphalangeal joint 104 is formed between the distal 101 and middle 103 phalanges, proximal interphalangeal joint 106 is formed between the middle 103 and proximal 105 phalanges, and the metatarsophalangeal joint 108 is formed between the proximal phalanx 105 and the metatarsal 107. The hammertoe deformity in the foot is apparent in the proximal interphalangeal joint 106.

A similar digital deformity condition in the hand is depicted in FIG. 1B. FIG. 1B depicts a human hand 110 afflicted with mallet finger deformity. Distal phalanx 111, middle phalanx 113, proximal phalanx 115, and metacarpal 117 bones are depicted in hand 110. The distal interphalangeal joint 114 is formed between the distal 111 and middle 113 phalanges, the proximal interphalangeal joint 116 is formed between the middle 113 and proximal 115 phalanges, and the metacarpophalangeal joint 118 is formed between the proximal phalanx 115 and the metacarpal 117. The mallet finger deformity in the hand is apparent in the distal interphalangeal joint 114.

Early treatments for digital deformities include the use of strapping, taping, orthotics, or immobilization of the hand or the foot. However, once the deformity becomes fixed, surgical treatment will be necessary. Surgical treatments include bone fixation devices that fixate the bones in order to fuse them into a stable mass. These orthopedic implant devices realign bone segments and hold them together in compression until healing occurs, resulting in a stable mass. Typical implant devices include intramedullary nails, plates, rods and screws.

Infection and complications are a major concern in these procedures. Wound closure is technically demanding for the surgeon, and devices that add surface prominence, such as plates or exposed screws, add to the difficulty by requiring greater tissue tension during incision reapproximation. This increases the risk of post-operative wound infections and dehiscence that may ultimately result in limb amputation. While there exist less intrusive devices, many devices lack the application of compression forces to the bone, causing the treated bones to eventually become misaligned from the desired position.

There is therefore a need for improvements in intramedullary fixation implants and methods of use that overcome some or all of the previously described drawbacks of prior fixation assemblies and processes.

SUMMARY OF THE INVENTION

The present invention is improved devices and methods for bone fixation.

The improved devices include an intramedullary fixation implant for joining bones and translating compression between the bones for treating various digital deformities. In a preferred embodiment, the intramedullary fixation implant comprises a first fixation portion and a second fixation portion connected to the first fixation portion, wherein the second fixation portion comprises a first projection and a second projection separated by a slot, wherein the first projection and the second projection comprise a plurality of barbs shaped and arranged along the first and second projections such that they cooperatively form a thread along the second fixation portion.

Broadly, the methods of the invention for joining and compressing a first bone to a second bone of a joint comprise: creating a first hole in the first bone, creating a second hole in the second bone, advancing the first fixation portion of the intramedullary fixation implant into the second hole in the second bone, counter-rotating the second bone, pressing the second fixation portion of the intramedullary fixation implant linearly into the first hole in the first bone, and rotating the second bone into a final fixation position.

Instruments are also disclosed for use in practicing the invention. These include an implant driving tool for driving the first fixation portion into the second hole in the second bone.

Numerous variations may be practiced in the preferred embodiment.

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems, methods, and apparati for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended hereto or as subsequently amended, but merely to clarify and exemplify the invention.

FIG. 3B is a front view of the intramedullary fixation implant shown in FIG. 3A according to the preferred embodiment of the invention;

FIG. 3C is a side view of the intramedullary fixation implant shown in FIG. 3A according to the preferred embodiment of the invention;

FIG. 3D is a top view of the intramedullary fixation implant shown in FIG. 3A according to the preferred embodiment of the invention;

FIG. 3E is a bottom view of the intramedullary fixation implant shown in FIG. 3A according to the preferred embodiment of the invention;

DETAILED DESCRIPTION OF THE INVENTION

The invention may be understood more readily by reference to the following detailed description of a preferred embodiment of the invention. However, techniques, systems, and operating structures in accordance with the invention may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1A:
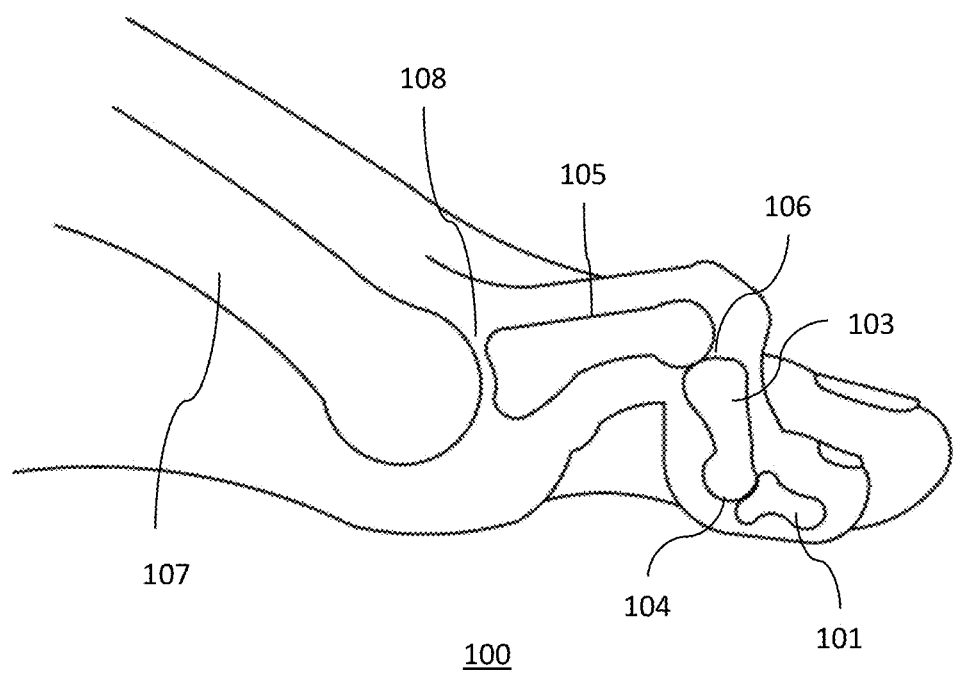
FIG. 1A depicts a human foot afflicted with hammertoe deformity.
Figure 1B:
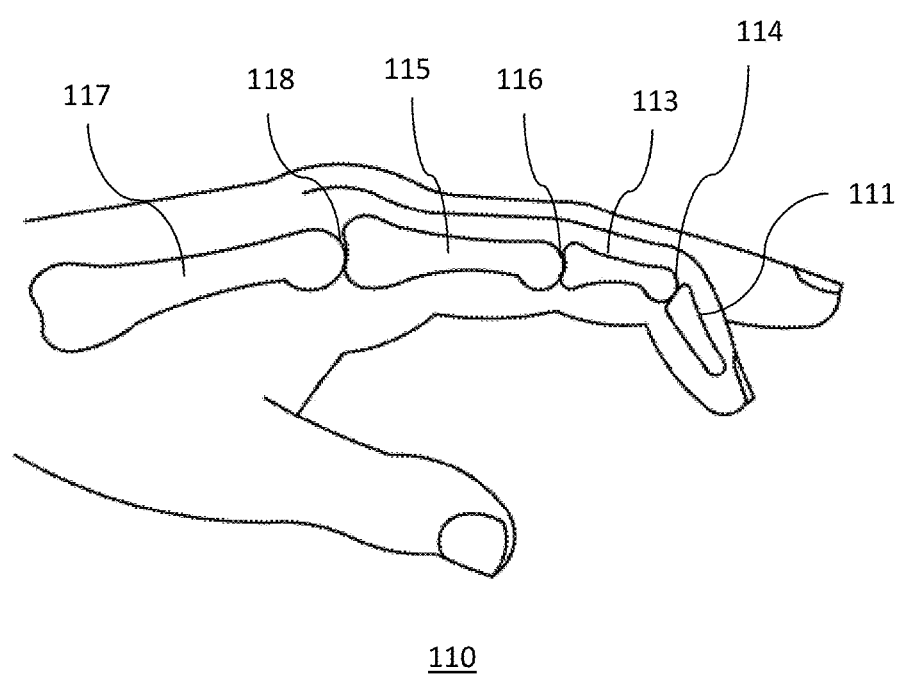
FIG. 1B depicts a human hand afflicted with mallet finger deformity.

The intramedullary fixation implant of present invention is described with reference to the treatment of a hammertoe deformity illustrated in FIG. 1A. However, it should be appreciated that the present invention may be used to treat any other digital deformities, including, but not limited to claw toes, mallet toes, bone spurs, overlapping and underlapping toes, mallet fingers, jersey fingers, coach's fingers, and the like. As such, the present invention may be utilized for the fixation of the following bones in the foot shown in FIG. 1A: distal phalanx 101 to the middle phalanx 103 in the distal interphalangeal joint 104, middle phalanx 103 to the proximal phalanx 105 in the proximal interphalangeal joint 106, or the proximal phalanx 105 to the metatarsal 107 in the metatarsophalangeal joint 108. Similarly, the present invention may be utilized for the fixation of the following bones in the hand shown in FIG. 1B: distal phalanx 111 to the middle phalanx 113 in the distal interphalangeal joint 114, middle phalanx 113 to the proximal phalanx 115 in the proximal interphalangeal joint 116, or proximal phalanx 115 to the metacarpal 117 in the metacarpophalangeal joint 118.

Figure 2:
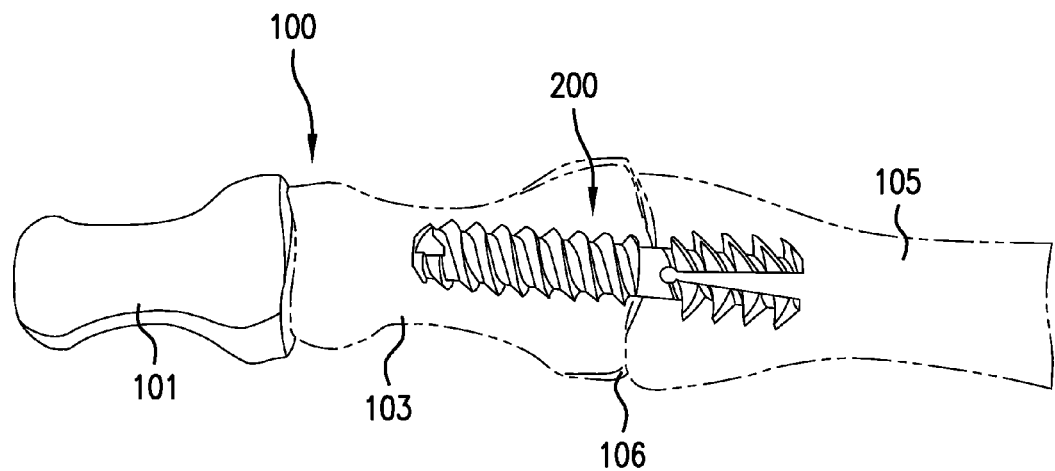
FIG. 2 is a perspective view of an intramedullary fixation implant of the present invention inserted into the bones of patient's foot according to the preferred embodiment of the invention.

Referring now to FIG. 2, there is shown an intramedullary fixation implant 200 that may be used in the practice of the present invention. As shown in FIG. 2, intramedullary fixation implant 200 may be used to join the middle phalanx 103 to the proximal phalanx 105 in the proximal interphalangeal joint 106 of foot 100. Intramedullary fixation implant 200 is used to translate compression between the middle phalanx 103 and the proximal phalanx 105 as will be further apparent below. Intramedullary fixation implant 200 may be made of PEEK (polyetheretherketone) material. The intramedullary fixation implant 200 is preferably made of radiolucent material, allowing for clear visualization of the fusion site. In other embodiments, intramedullary fixation implant 200 may be made of other materials known in the art, including other PAEK (polyaryletherketone) plastics, SST, titanium, NiTi, Cobalt chrome, polylactic acid, or other similar types of materials. Also, intramedullary fixation implant 200 may be coated with an osteoconductive material, such as, for example, plasma spray or other similar types of porous materials, that are capable of supporting or encouraging bone ingrowth into the material.

Figure 3A:
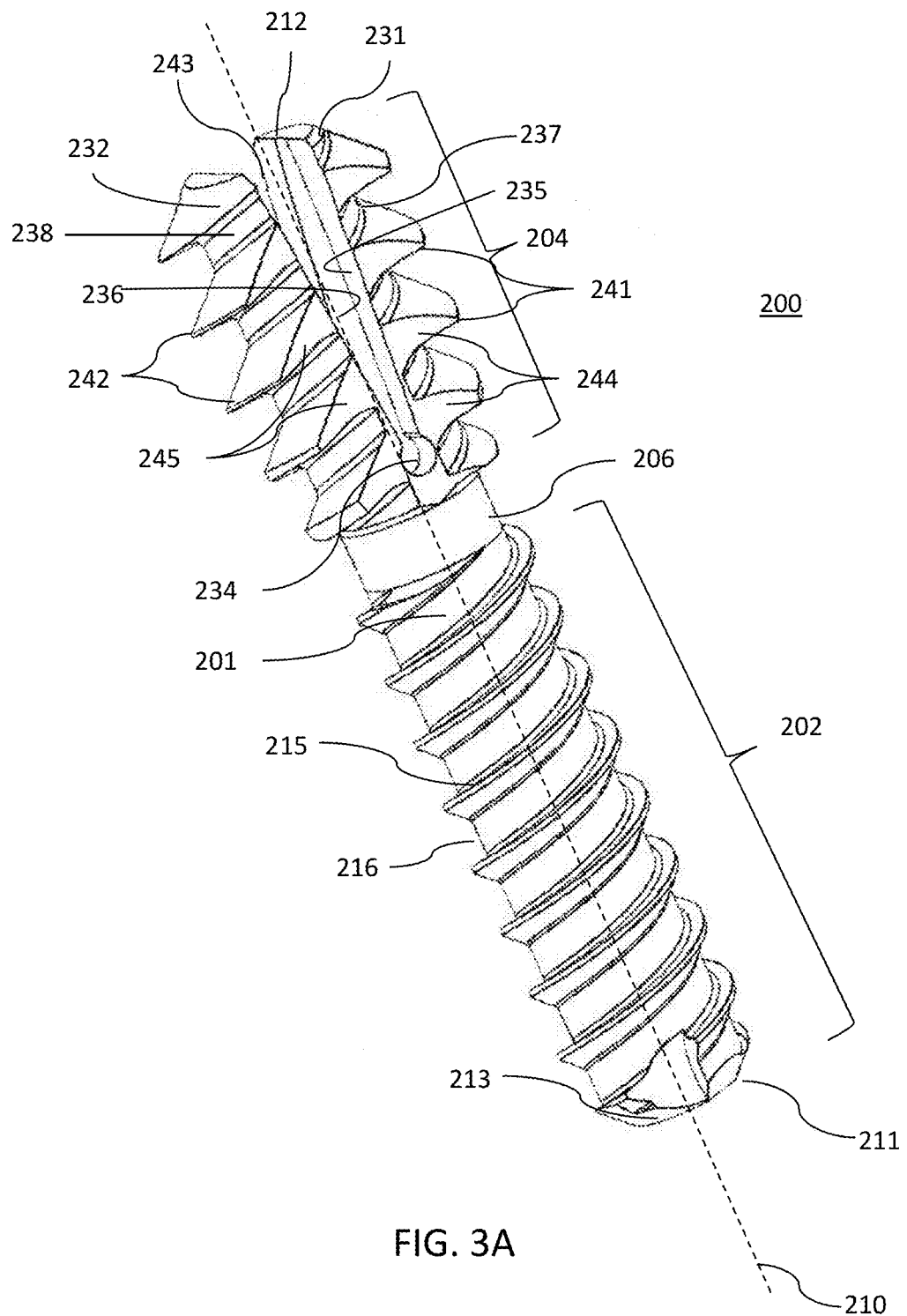
FIG. 3A is a perspective view of the intramedullary fixation implant of the present invention according to the preferred embodiment of the invention.

Intramedullary fixation implant 200 is shown in greater detail in FIGS. 3A-3E, where FIG. 3A is a perspective view of the intramedullary fixation implant 200, FIG. 3B is a front view thereof, FIG. 3C is a side view thereof, FIG. 3D is a top view thereof, and FIG. 3E is a bottom view thereof. As shown, intramedullary fixation implant 200 preferably comprises unitary elongated body 201 extending from a first end 211 to a second end 212 along longitudinal axis 210. Intramedullary fixation implant 200 further comprises a first fixation portion 202 at the first end 211 and a second fixation portion 204 at the second end 212 connected via middle portion 206.

The first fixation portion 202 of intramedullary fixation implant 200 is substantially cylindrical in shape. Alternatively, first fixation portion 202 may comprise a taper, with width that decreases from the middle portion 206 to the first end 211 (not shown). First fixation portion 202 preferably comprises on its exterior surface 216 threads 215. Threads 215 are preferably helical dual-lead threads. First fixation portion 202 may also be provided with a self-tapping leading edge 213 to provide portion 202 with the ability to remove bone material during insertion of the first fixation portion 202 into the bone.

The middle portion 206 is substantially cylindrical in shape or cross-section. However, the middle portion may comprise other shapes or cross-sections—it may have rectangular, square, or hexagonal shape or cross-section.

Figure 3F:
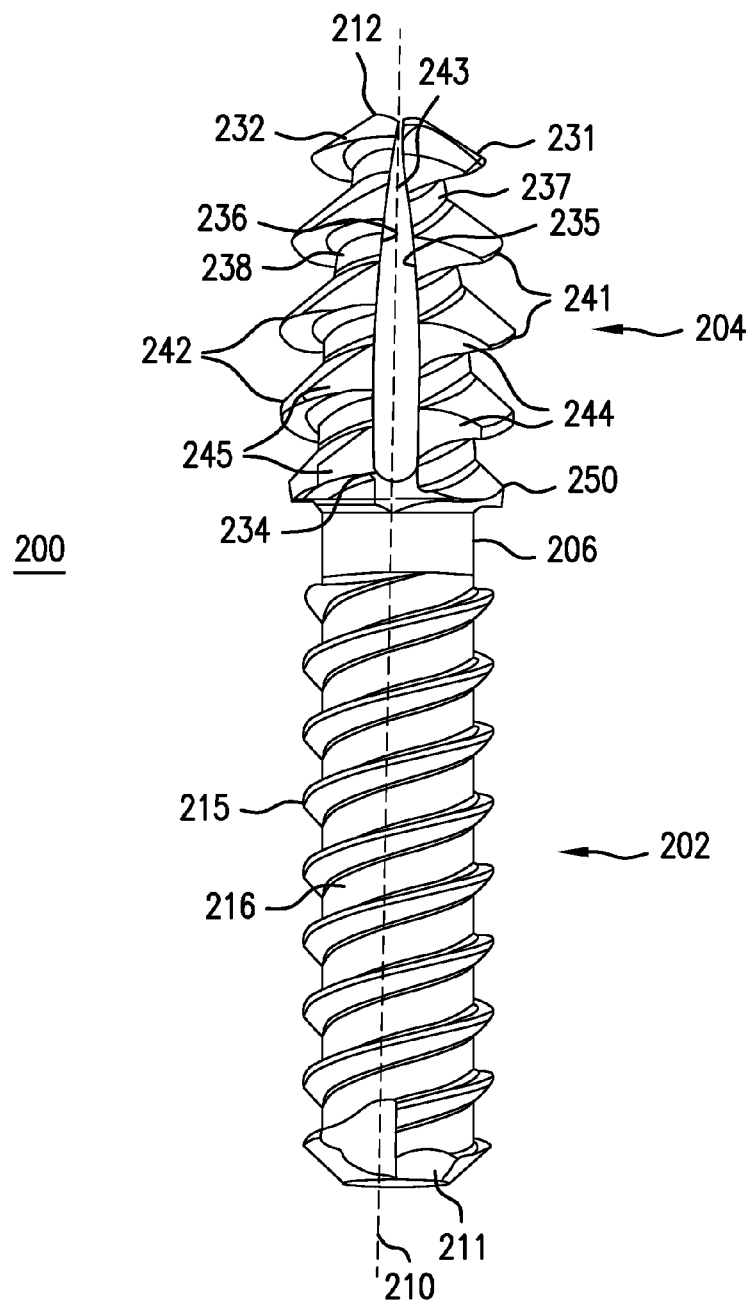
FIG. 3F is a side view of the intramedullary fixation implant shown in FIG. 3A in a collapsed position according to the preferred embodiment of the invention.
Figure 4:
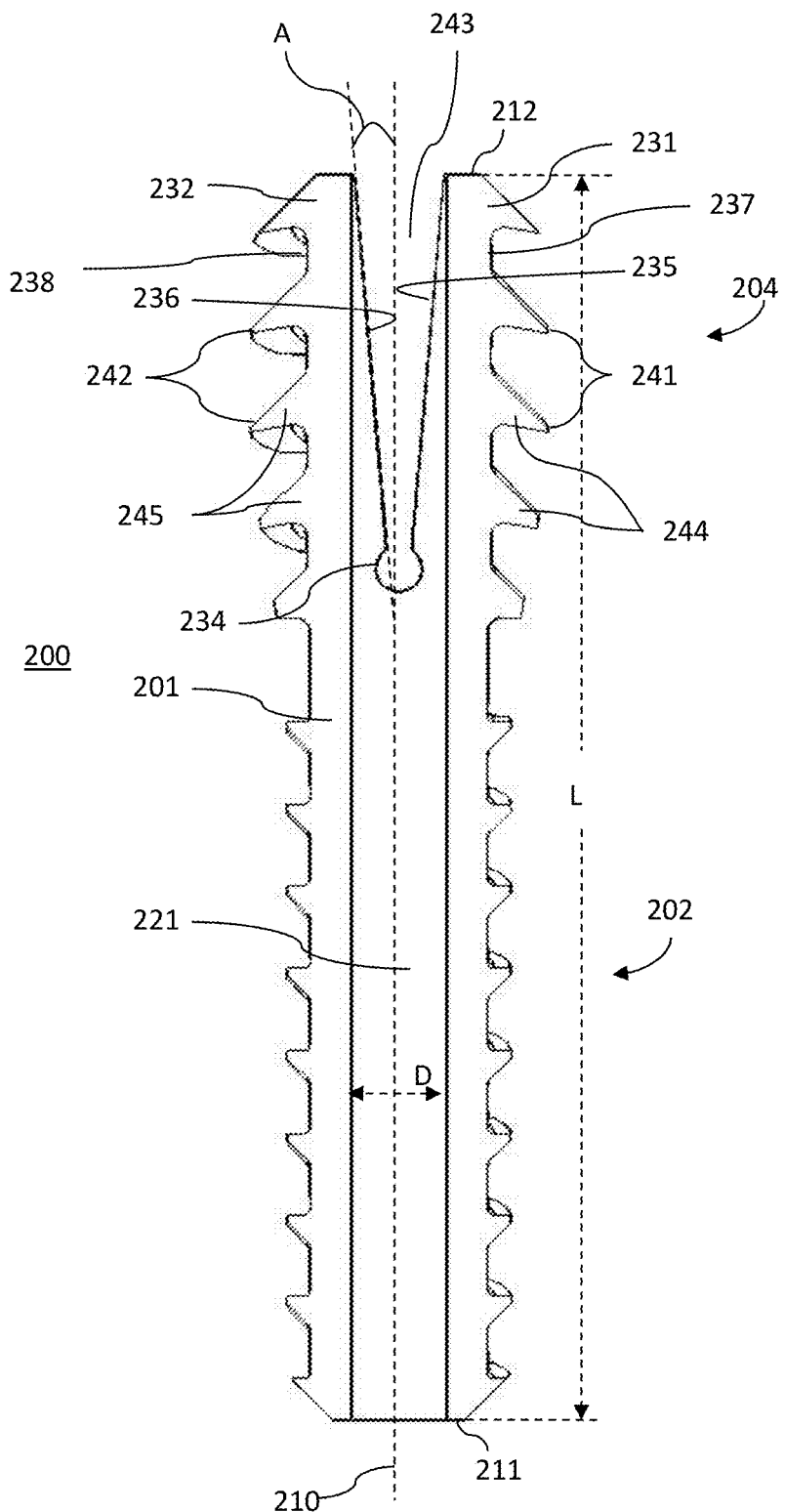
FIG. 4 is a cross-sectional view of the intramedullary fixation implant shown in FIGS. 3A-3E according to the preferred embodiment of the invention.

The second fixation portion 204 preferably comprises a first projection 231 and a second projection 232 extending from the middle portion 206 to the second end 212. Although two projections are illustrated, second fixation portion 204 may comprise three or four projections. FIG. 4 is the cross-sectional view of intramedullary fixation implant 200 taken along line 4-4 in FIG. 3D. As shown in FIG. 3B, and in further detail in FIG. 4, the first and second projections 231 and 232 further comprise oppositely-disposed outer-facing convex surfaces 237 and 238. In a preferred embodiment, outer facing convex surfaces 237 and 238 are substantially parallel to one another. Further, the first and second projections 231 and 232 preferably comprise oppositely-disposed inner-facing flat surfaces 235 and 236, longitudinally separated by a V-shaped slot 243. The oppositely-disposed inner-facing flat surfaces 235 and 236 are offset from the longitudinal axis 210 by angle A. Angle A is preferably in the range of about 0 degrees to about 45 degrees, more preferably from about 5 degrees to about 30 degrees, and more preferably it is about 10 degrees. Projections 231 and 232 are flexible such that they can be collapsed from a normal or open position shown in FIG. 4 to a collapsed position shown in FIG. 3F, where projections 231 and 232 are brought toward each other. In a collapsed position, inner-facing flat surfaces 235 and 236 are preferably substantially parallel to each other and to the longitudinal axis 210. As show in FIG. 4, second fixation portion 204 further comprises a circular compression notch 234 formed at the meeting-place of the first and second projections 231 and 232 at the inner-facing flat surfaces 235 and 236. Circular compression notch 234 assists in allowing projections 231 and 232 to compress towards each other.

The first and second projections 231 and 232 further comprise a plurality of barbs 241 and 242, respectively. In a preferred embodiment, first and second projections 231 and 232 each comprise five barbs 241 and 242, respectively. Barbs 241 and 242 extend outwardly from the outer-facing convex surfaces 237 and 238 of first and second projections 231 and 232, respectively, away from the longitudinal axis 210. Barbs 241 of the first projection 231 and barbs 242 of the second projection 232 are shaped and arranged along the outer-facing surfaces 237 and 238, respectively, such that they coextensively or cooperatively form a helical thread 250 along the second fixation portion 204. As a result, barbs 241 of the first projection 231 and the barbs 242 of the second projection 232 are asymmetrically disposed. In the preferred embodiment, the helical thread 250 comprises a reverse-buttress thread that causes the second fixation portion 204 to be better secured to a bone against the force of deflection. The helical thread 250 formed by barbs 241 and 242 is used to translate compression between two bones, such as the middle phalanx 103 and proximal phalanx 105, by applying torque to the intramedullary fixation implant 200 as will be later described.

As shown in FIG. 4, the elongated body 201 comprises length L. In a preferred embodiment, length L is in the range of approximately 13.5 millimeters (mm) to approximately 15 mm. First fixation portion 202 comprises length L1 and major diameter 1 d, while second fixation portion 204 comprises length L2 and major diameter 2 d. In a preferred embodiment, length L1 is in the range of approximately 6.5 mm to approximately 7.0 mm, length L2 is in the range of approximately 5.5 mm to approximately 6.8 mm, major diameter 1 d is in the range of approximately 2.8 mm to approximately 4.0 mm, and major diameter 2 d is in the range of approximately 4.0 mm to approximately 5.5 mm. The size and length of the intramedullary fixation implant 200 that may be used in the practice of the invention can vary considerably depending on the size of the bones that are being joined and the surgeon's preferences. Intramedullary fixation implant 200 is cannulated along length L having a bore 221 aligned along longitudinal axis 210 and extending from first end 211 to second end 212. Bore 221 comprises diameter D provided to interact with a guide wire or a Kirschner wire (K-wire) by receiving the K-wire within the bore 221 as will be later described. Preferably, diameter D is constant throughout length L of intramedullary fixation implant 200 when projections 231 and 231 are in a normal or open position. Different diameters and K-wire sizes may be used depending on the diameter of the bones that are being joined and the surgeon's preferences. Illustratively, the diameter of the K-wire is in the range of approximately 0.7 mm to approximately 4.0 mm, and more preferably approximately 0.9 mm to approximately 1.6 mm. In a preferred embodiment, intramedullary fixation implant 200 comprises various sizes to accommodate variations in bone sizes. For example, the intramedullary fixation implant 200 may be available in the following three sizes and dimensions:

TABLE 1

| Size | Small | Medium | Large |
| --- | --- | --- | --- |
| Overall length L (mm) | 13.5 | 15 | 15 |
| First fixation portion length L1 | 6.5 | 7.0 | 7.0 |
| Second fixation portion length L2 | 5.5 | 6.8 | 6.8 |
| Major diameter 1d (mm) | 2.8 | 3.4 | 4.0 |
| Major diameter 2d (mm) | 4.0 | 4.5 | 5.5 |
| Guide wire (mm) compatibility | 1.1 | 1.4 | 1.6 |

The first fixation portion 202 and second fixation portion 204, shown in FIG. 3C, are disposed along longitudinal axis 210. In alternative embodiment, second fixation portion 204 may be offset from the longitudinal axis 210 and from the first fixation portion 202 at an angle (not shown). Such an angle will determine the angle of the bone fixation. Preferably, the second fixation portion 204 may be offset from the longitudinal axis 210 at an angle between about 0 degrees and about 30 degrees, and more preferably between about 5 degrees and about 10 degrees. During operation, a surgeon may select an intramedullary fixation implant 200 having a desired angle to adopt the intramedullary fixation implant 200 to the implantation site.

As shown in FIGS. 3B and 3D, each barb 241 and 242 further comprises opposing flat side walls 244 and 245, respectively. As a result, the second fixation portion 204 comprises a cross section having oppositely disposed convex edges 301 and oppositely disposed flat edges 302. Opposing flat side walls 244 and 245, and thereby oppositely disposed flat edges 302, are provided to engage with an implant driving tool as described below.

Figure 5A:
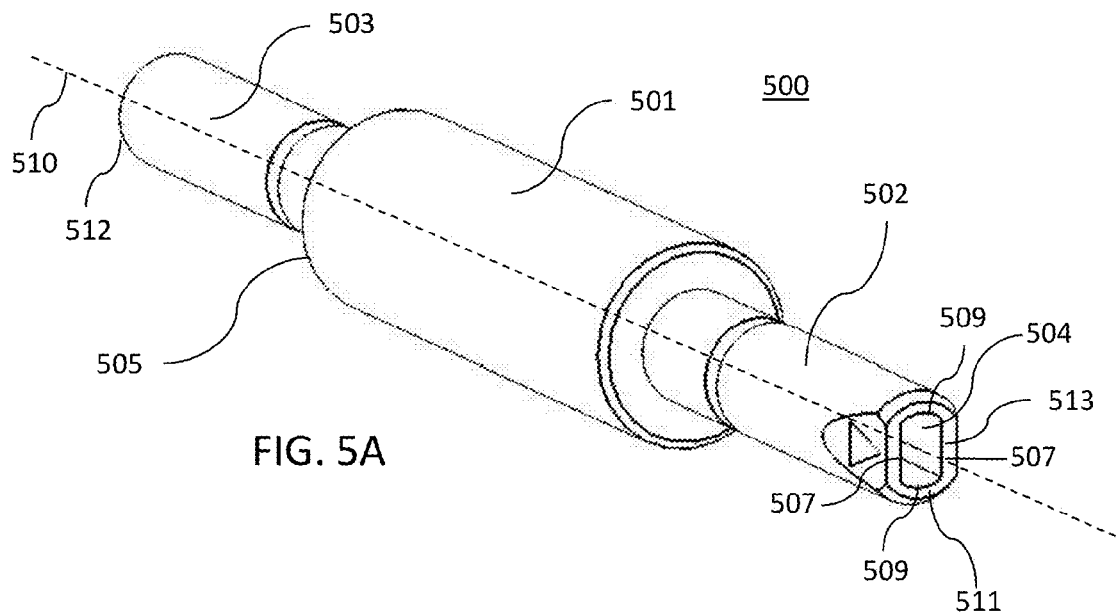
FIG. 5A is a perspective view of an implant driving tool according to the preferred embodiment of the invention.
Figure 5B:
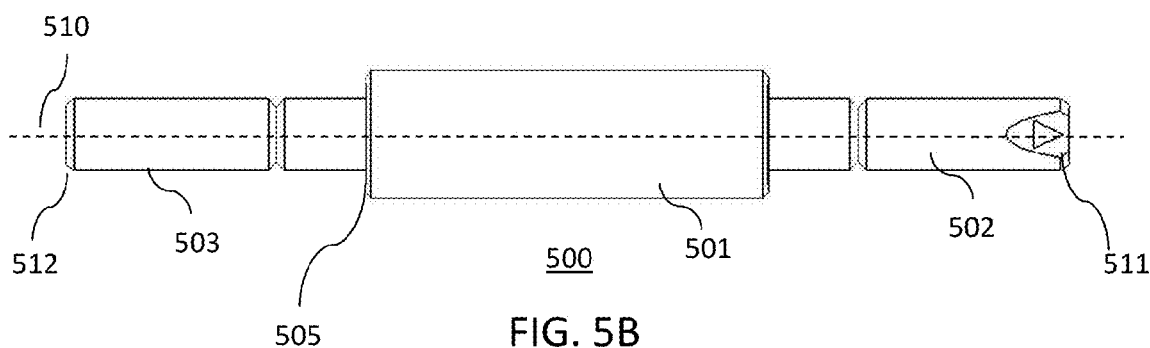
FIG. 5B is a side view of the implant driving tool shown in FIG. 5A according to the preferred embodiment of the invention.
Figure 5C:
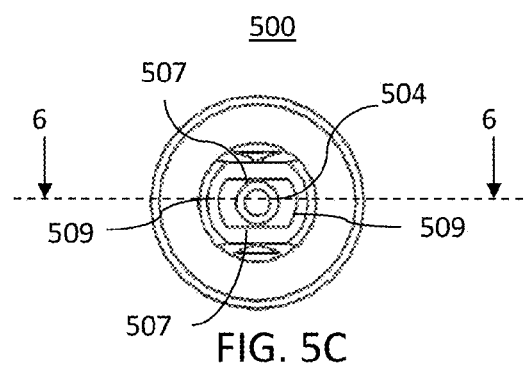
FIG. 5C is a front view of the implant driving tool shown in FIG. 5A according to the preferred embodiment of the invention.
Figure 6A:
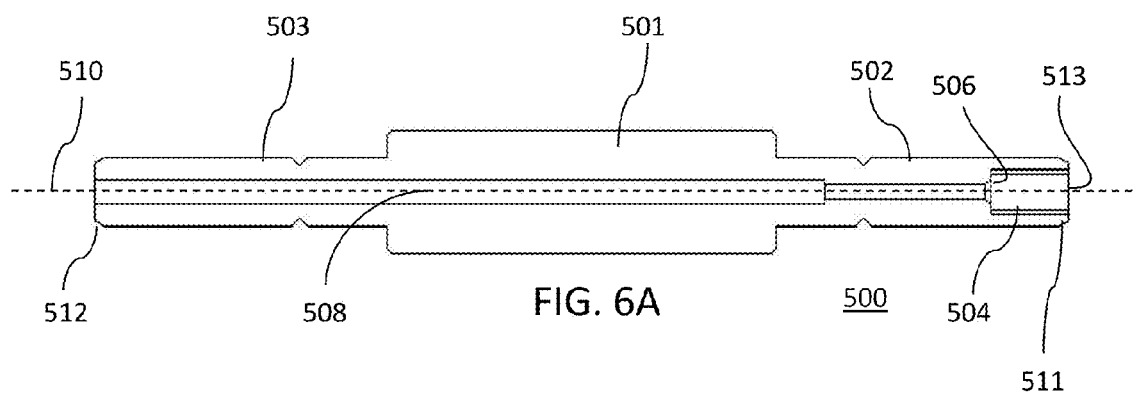
FIG. 6A is a cross-sectional view of the implant driving tool shown in FIGS. 5A-5C according to the preferred embodiment of the invention.

FIGS. 5A-5C illustrate a preferred embodiment of an implant driving tool 500 used to drive the intramedullary fixation implant 200 into the bone of fixation. FIG. 5A illustrates the prospective view of the implant driving tool, FIG. 5B illustrates a side view thereof, and FIG. 5C illustrates the front view thereof. FIG. 6A illustrate the cross section of the implant driving tool taken along line 6-6 in FIG. 5C. Implant driving tool 500 comprises an elongated body 505 extending from a first end 511 to a second end 512 along a longitudinal axis 510. The implant driving tool 500 further comprises a handle portion 501 disposed between an implant receiving portion 502 at the first end 511 and an end portion 503 at the second end. Handle portion 501 may be ribbed (not shown) or may comprise friction resistant material to assist the surgeon to manually apply torque to the implant driving tool 500. Alternatively, or in addition, end portion 503 may be sized to receive a torque transmitting tool (not show). As shown in FIG. 6A, implant driving tool 500 is cannulated having a bore 508 extending along longitudinal axis 510 of elongated body 505.

Figure 6B:
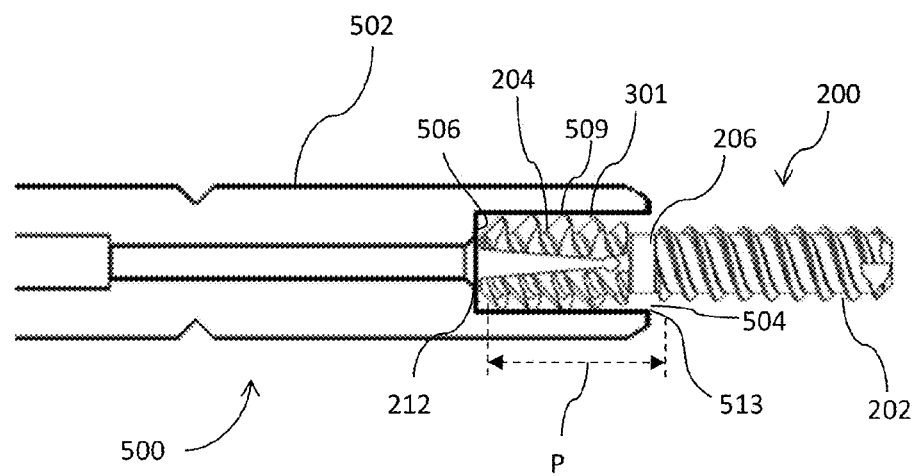
FIG. 6B is an enlarged cross-sectional view of the implant driving tool shown in FIGS. 5A-5C used with the intramedullary fixation implant shown in FIGS. 3A-3E according to the preferred embodiment of the invention.

Implant receiving portion 502 preferably comprises an aperture 504 at the first end 511 of the implant driving tool 500. Aperture 504 extends from an open end 513 at the first end 511 of the implant driving tool 500 to an inner base wall 506. In a preferred embodiment, aperture 504 is sized for receiving the second fixation portion 204 of intramedullary fixation implant 200 in a normal or open position as shown in FIG. 6B. Aperture 504 comprises a cross section that complements the cross section of the second fixation portion 204. As shown in FIGS. 5A and 5C, aperture 504 comprises oppositely disposed inner flat side walls 507 and oppositely disposed inner concave side walls 509. When the second fixation portion 204 of the intramedullary fixation implant 200 is inserted into aperture 504, as shown in FIG. 6B, second fixation portion 204 is aligned with aperture 504 such that oppositely disposed convex edges 301 are disposed against the concave side walls 509 of aperture 504, and the oppositely disposed flat edges 302 are disposed against the oppositely disposed flat side walls 507 (not shown). Aperture 504 further comprises depth P sufficient to receive the second fixation portion 204. The inner base wall 506 prevents the intramedullary fixation implant 200 from over insertion into aperture 504 of implant driving tool 500. When the second fixation portion 204 is inserted into aperture 504, the second end 212 of the intramedullary fixation implant 200 abuts the inner base wall 506 of aperture 504. In a preferred embodiment, aperture 504 comprises depth P equal to the length of the second fixation portion 204 plus the length of the middle portion 206 of the intramedullary fixation implant 200 such that the first fixation portion 202 is not inhibited by aperture 504 when the second fixation portion 204 is fully inserted into aperture 504 of the implant driving tool 500. Implant receiving portion 502 of the implant driving tool 500 may further comprise a pair of indicators 514, such as arrows, on opposite sides of its outer surface, parallel to the oppositely disposed inner flat side walls 507. Indicators 514 are used to align the intramedullary fixation implant 200 with the bones as will be later described.

Figure 7:
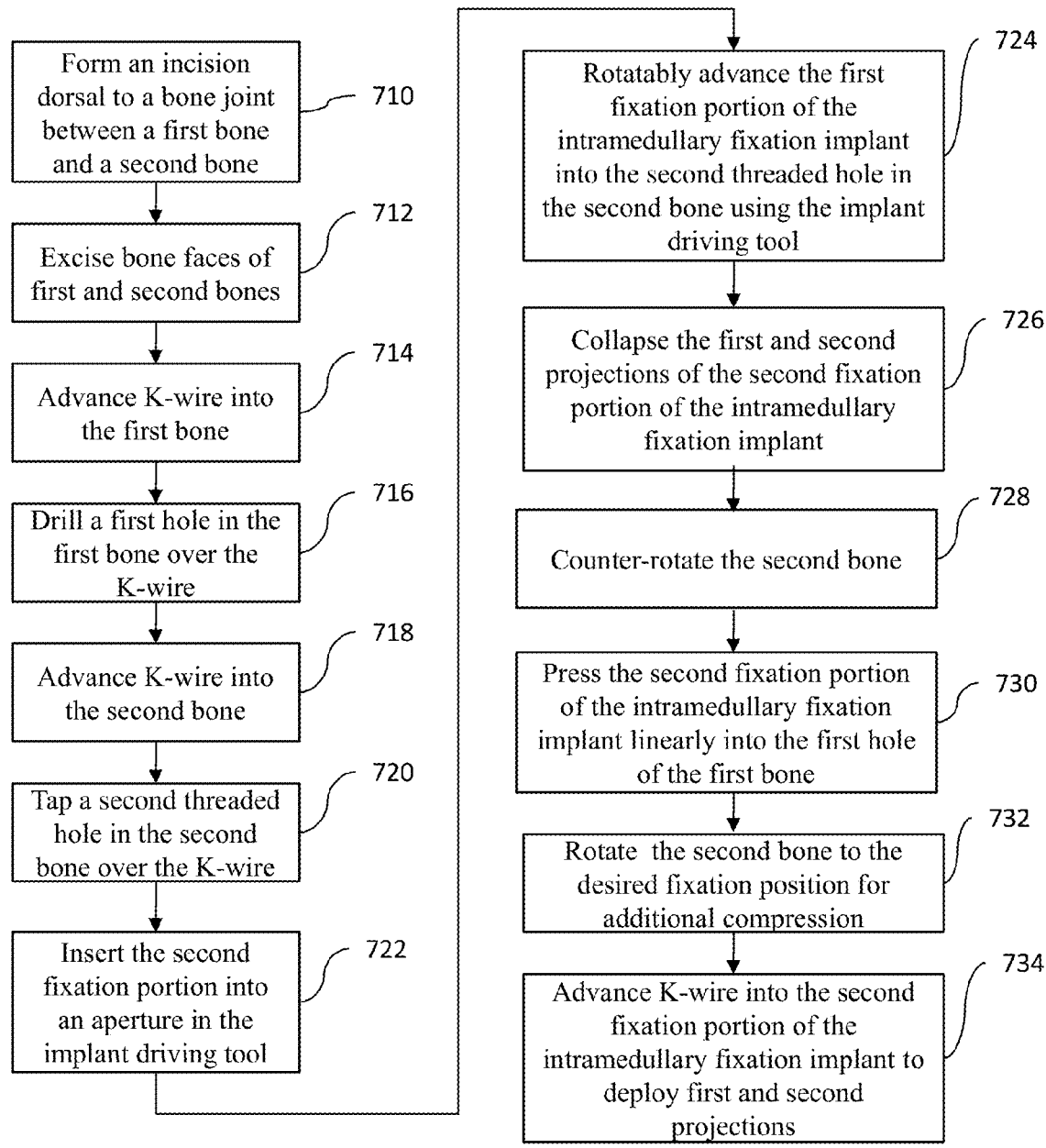
FIG. 7 is a flow chart depicting illustrative steps of an embodiment of the invention.
Figure 8A:
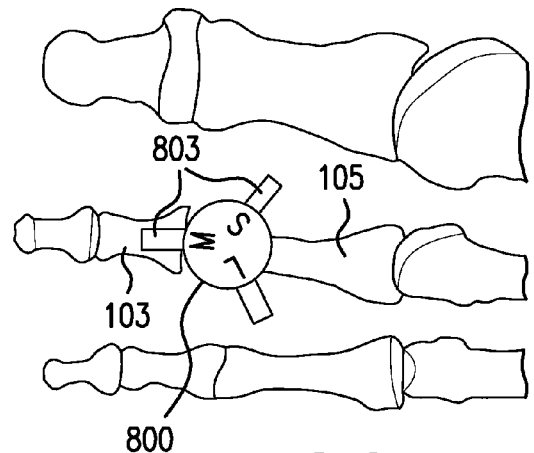
FIGS. 8A-8P depict details of certain steps of FIG. 7.
Figure 8B:
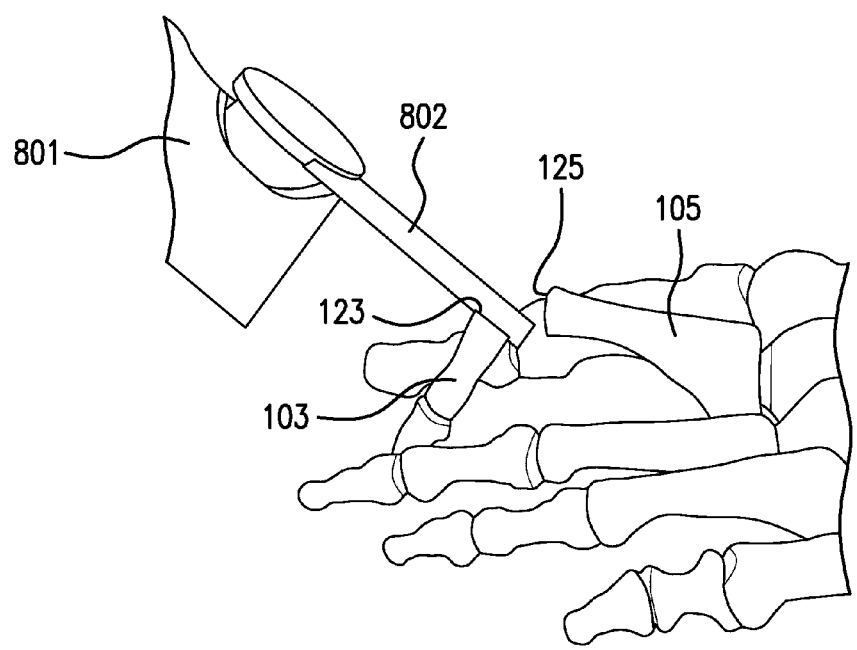
Figure 8C:
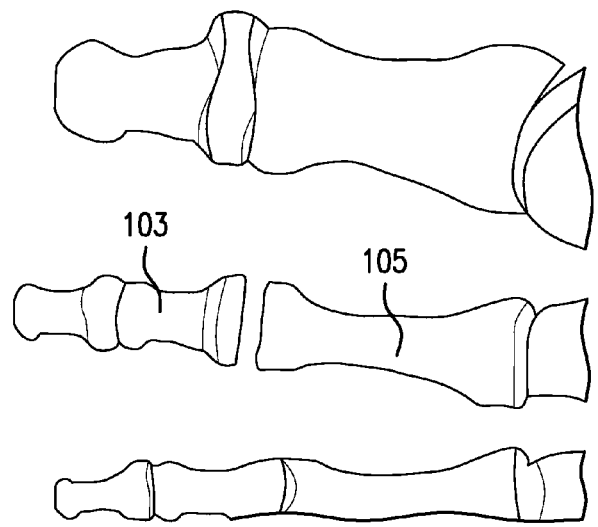
Figure 8D:
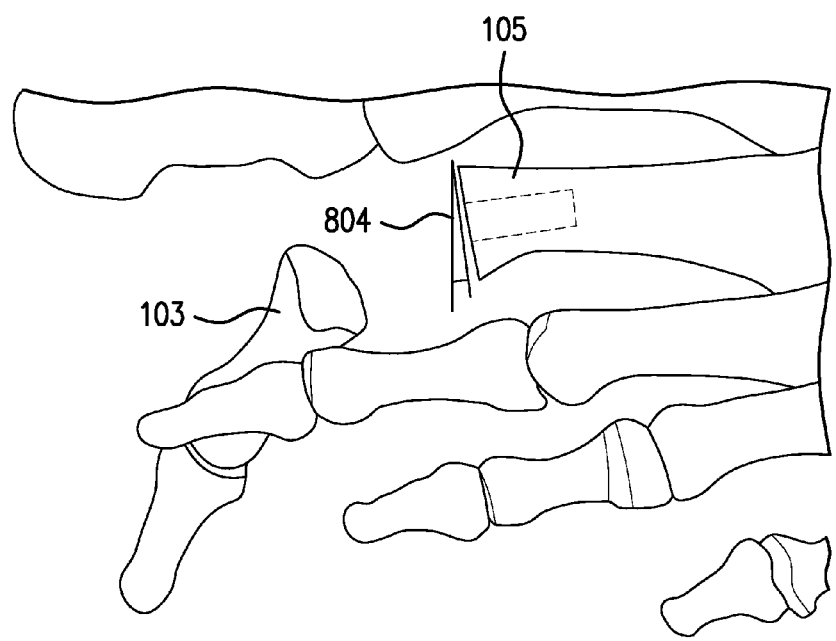

The intramedullary fixation implant 200 of the present invention is utilized to join two bones together, such as a first bone and a second bone, and to translate compression between the bones. FIGS. 7 and 8A-8P depict illustrative operative technique of an embodiment of the invention used to treat hammertoe deformity between the proximal phalanx 105 (i.e., a first bone) and the middle phalanx 103 (i.e., a second bone) in the proximal interphalangeal joint 106. It will be understood that the operative technique is only illustrative, that the order of execution of some steps may vary, and that some steps may not need to be used in the treatment of a particular patient in accordance with the invention.

As shown in FIG. 8A, before beginning the operative procedure, an intra-operative template 800 may be used to determine the optimal implant size. This template 800 is radiopaque and can be used with fluoroscopy. Template 800 may comprise a plurality of rectangular extensions 803 each corresponding to a differently sized intramedullary fixation implant 200. In this example, three rectangular extensions 803 are used corresponding to a small, medium, and large sized intramedullary fixation implant 200. The length and width of each rectangular extension 803 correspond to the length and major diameter of the threaded end of the implant for the middle phalanx 103. Each rectangular extension 803 is aligned with the middle phalanx 103 by the surgeon to determine the optimal implant size.

After a proper implant size is chosen, in step 710 an incision is made in the foot over the dorsal aspect of the proximal interphalangeal joint 106, while soft tissue is released as necessary, so as to provide a complete visualization of the articular surfaces of the middle and proximal phalanges. The incision may be a dorsal longitudinal incision or a two semi-elliptical incision. As shown in FIG. 8B, the distal aspect or face 125 of the proximal phalanx 105 and the proximal aspect or face 123 of the middle phalanx 103 are excised in step 712 using blade 802 of cutting tool 801. In a preferred embodiment, the distal aspect of the proximal phalanx 105 is resected just posterior to the head of the phalange as either a straight cut (FIG. 8C), or at an angle 804 (FIG. 8D). Such an angle 804 will determine the angle of the bone fixation. Preferably, angle 804 is in a range of between about 0 degrees and about 30 degrees, and more preferably between about 5 degrees and about 10 degrees. In a preferred embodiment, angle 804 is approximately 10 degrees. The articular cartilage of the middle phalanx 103 may be denuded. In an alternative embodiment, the middle phalanx 103 can be also resected.

Figure 8E:
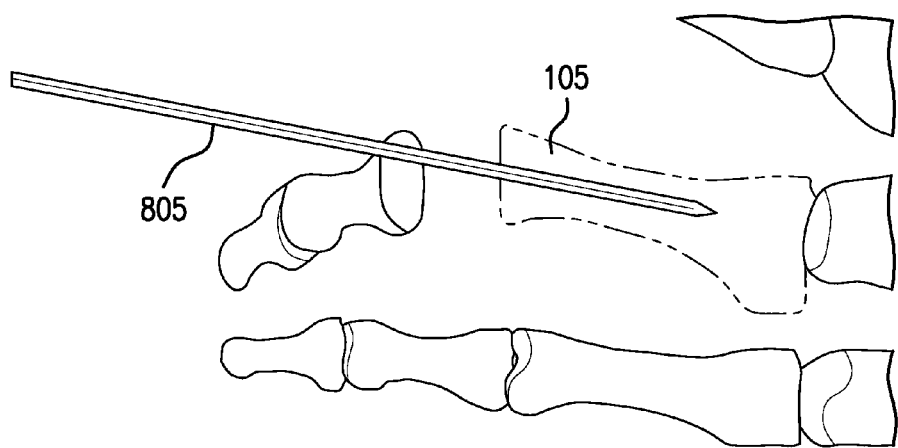
Figure 8F:
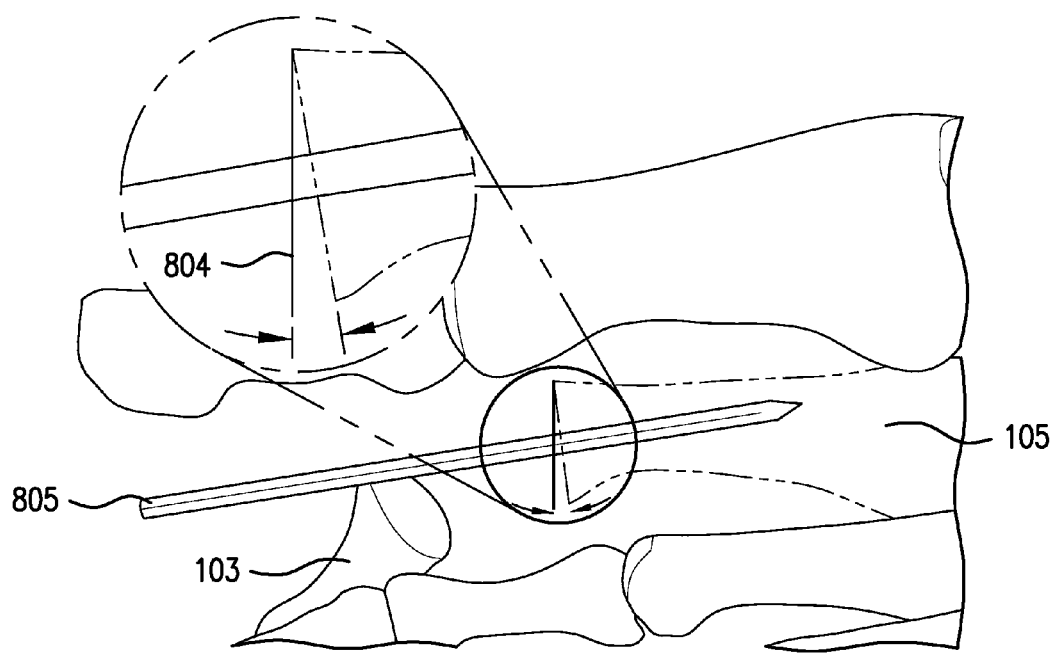
Figure 8G:
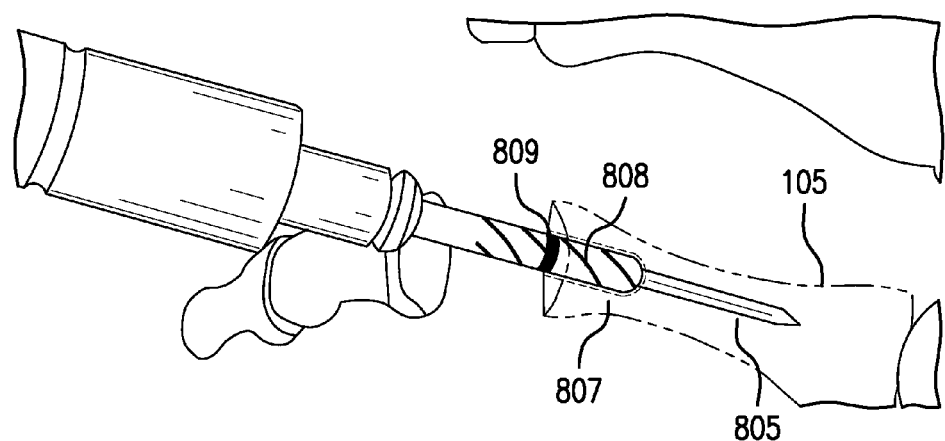

In step 714, a retrograde K-wire 805 is advanced into the proximal phalanx 105 along its central axis as shown in FIG. 8E, approximately 10 mm in depth. The K-wire 805 is advanced by the surgeon in a direction of the desired alignment of the intramedullary fixation implant 200 with respect to the proximal phalanx 105. As shown in FIG. 8F, If the proximal phalanx 105 was resected at an angle 804, the guide wire 805 is placed perpendicular to the resection of the proximal phalanx 105. Then in step 716, as shown in FIG. 8G, the proximal phalanx 105 is drilled using drill bit 808 over the K-wire 805 to create a hole 807 in the proximal phalanx 105. The K-wire 805 is used to guide drill bit 808 into the desired alignment. Accordingly, the drill bit 808 used in the present invention is preferably cannulated such that it may fit over the K-wire 805. The drill bit 808 may be driven manually or via a torque transmitting tool (not shown). The drill bit 808 may comprise a pre-marked depth line marking 809 to indicate how deep to advance the drill bit 808 into the proximal phalanx 105. The K-wire 805 is then removed from the proximal phalanx 105.

Figure 8H:
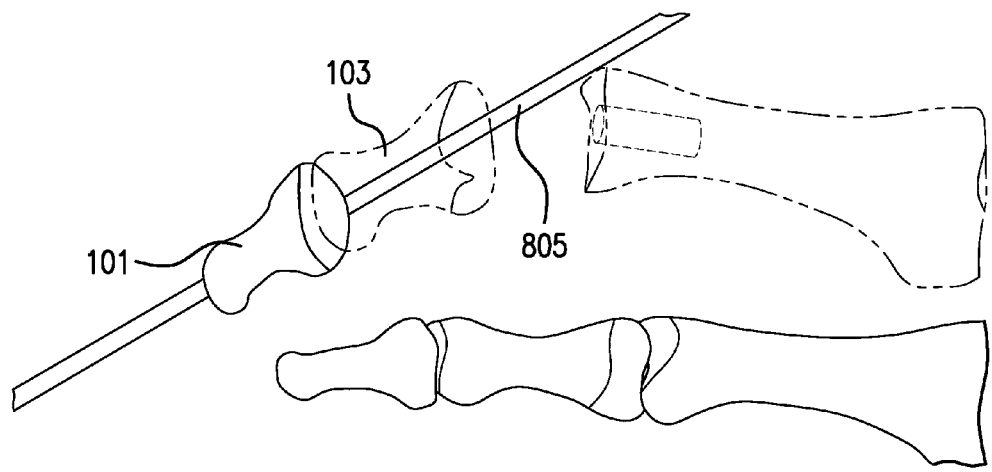
Figure 8I:
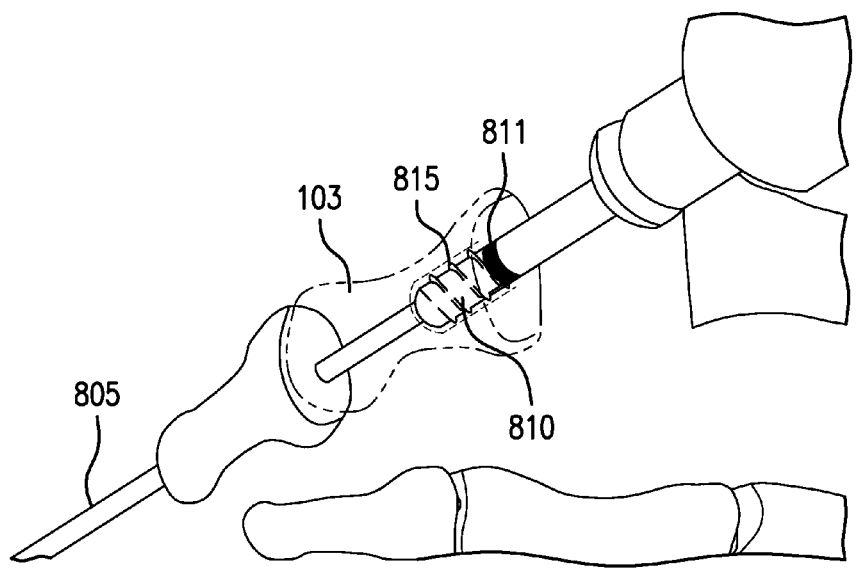

In step 718, as shown in FIG. 8H the K-wire 805 is advanced into the middle phalanx 103, through the distal phalanx 101, until the K-wire 805 exits the toe. In a preferred embodiment, the K-wire 805 is advanced into the middle phalanx 103 until a minimum of approximately 10 mm of K-wire 805 extends out of the middle phalanx 103. The same K-wire 805 may be used that was previously used in FIGS. 8E-8G. Alternatively, the surgeon can use a different K-wire. The K-wire 805 is advanced by the surgeon in a direction of the desired alignment of the intramedullary fixation implant 200 with respect to the middle phalanx 103. In step 720, as shown in FIG. 8I, the middle phalanx 103 is tapped over the K-wire 805 to create a threaded hole 815 in the middle phalanx 103 using tap 810 driven either manually or by a torque transmitting tool (not shown). The K-wire 805 is used to guide tap 810 into the desired alignment. Accordingly, tap 810 used in the present invention is preferably cannulated such that is may fit over the K-wire 805. Threaded hole 815 comprises threads that correspond to threads 215 of the first fixation portion 202. Guide tap 810 may comprise a depth line marking 811 to indicate how deep to advance the guide tap 810 into the middle phalanx 103.

Figure 8J:
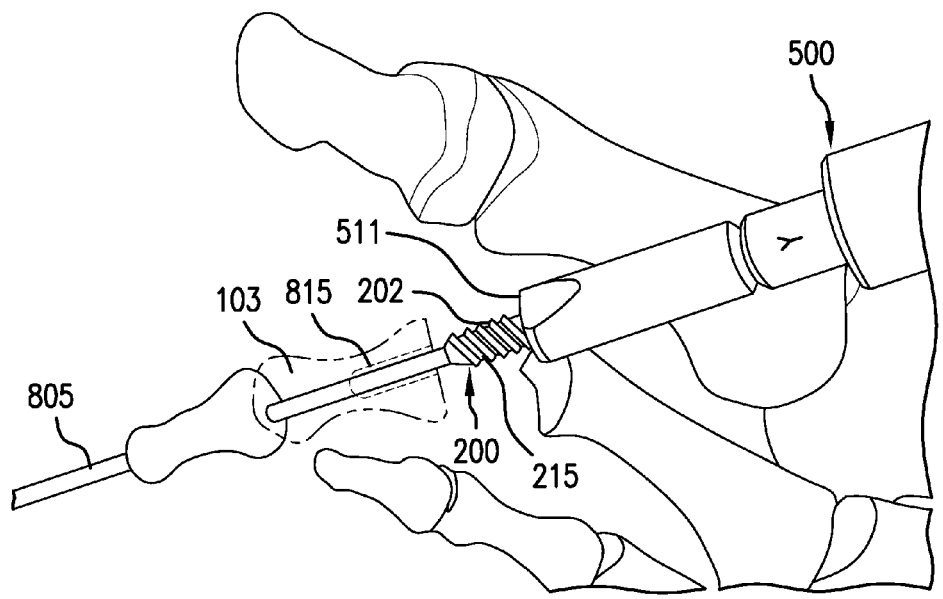
Figure 8K:
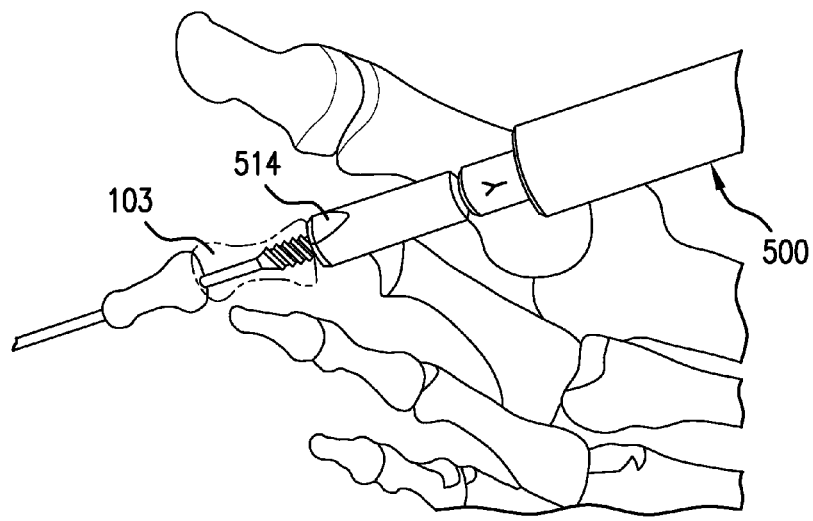

Next, in step 722, the second fixation portion 204 of intramedullary fixation member 200 is inserted into aperture 504 of the implant driving tool 500 as shown in FIG. 6B. As shown in FIG. 8J, in step 724, the first fixation portion 202 is rotatably advanced into the threaded hole 815 in the middle phalanx 103 over the K-wire 805 using the implant driving tool 500. As such, the K-wire 805 is advanced into bore 221 of the intramedullary fixation implant 200. The diameter of K-wire 805 that may be used in the practice of the present invention preferably is adapted to fit within diameter D of bore 221 of intramedullary fixation implant 200. The first fixation portion 202 may be advanced manually into the threaded hole 815 by rotating the handle 501 of the implant driving tool 500 or by attaching a torque transmitting tool to end portion 503 of the implant driving tool 500 (not shown). Threads 215 engage the threads tapped into the threaded hole 815. In an alternative embodiment, the middle phalanx 103 is not pre-tapped. It may be only pre-drilled or the intramedullary fixation implant 200 may be advanced into the middle phalanx 103 using the self-tapping leading edge 213. The first fixation portion 202 is rotatably advanced into the threaded hole 815 in the middle phalanx 103 until the first end 511 of the implant driving tool 500 meets the middle phalanx 103. This will ensure that the first fixation portion 202 is within the middle phalanx 103, leaving the unthreaded middle portion 206 (FIG. 6B) of the implant at the bone-to-bone interface. After the first fixation portion 202 is fully inserted into the middle phalanx 103 as desired, as shown in FIG. 8K, the implant driving tool 500 is oriented so that an indicator 514 of the implant driving tool 500 is aligned with the dorsal aspect of the middle phalanx 103 (12 o'clock position). This ensures the proper orientation of the implant in the phalanx. Then, the implant driving tool 500 is removed from the second fixation portion 204.

Figure 8L:
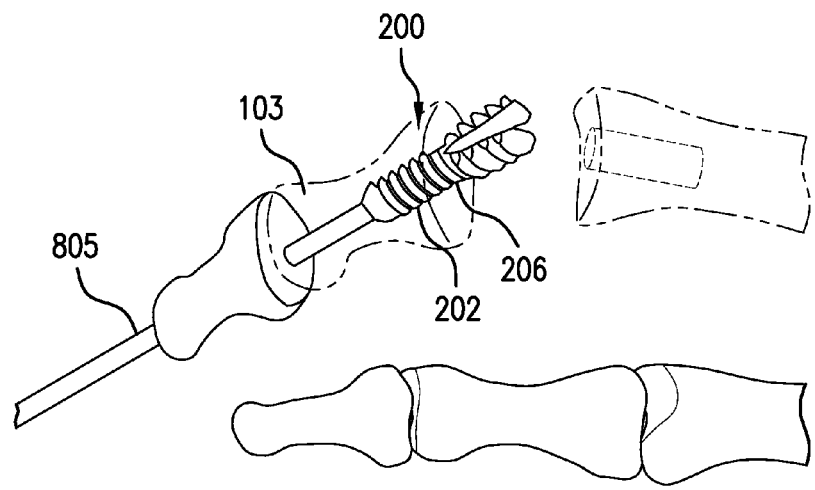
Figure 8M:
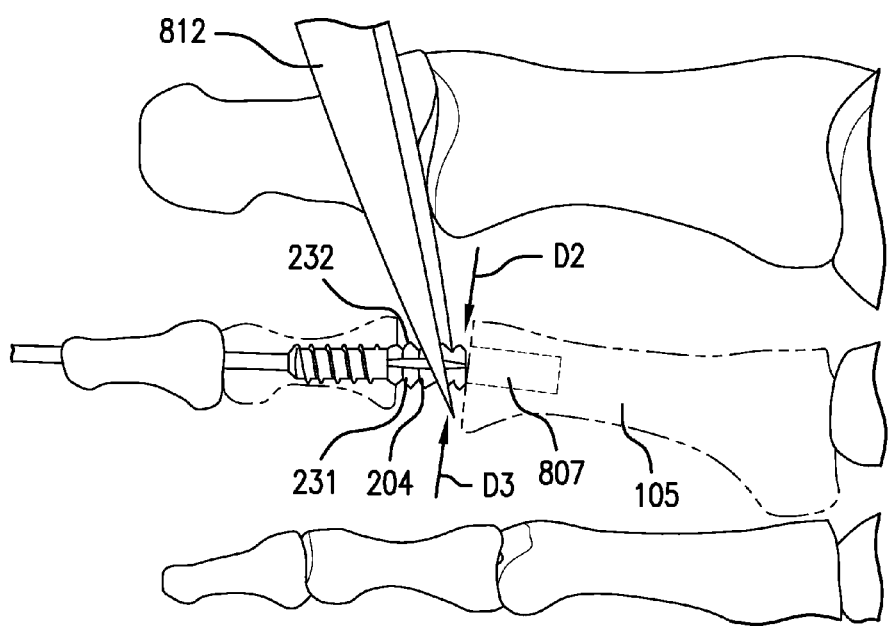

As shown in FIG. 8L, the K-wire 805 is pulled further into middle phalanx 103 until it is housed within the first fixation portion 202 and does not extend past the middle portion 206 of intramedullary fixation implant 200. In step 726, the first and second projections 231 and 232 of second fixation portion 204 are collapsed in directions D2 and D3 to a collapsed position shown in FIG. 3F. The first and second projections 231 and 232 may be collapsed by being compressed with forceps 812.

Figure 8N:
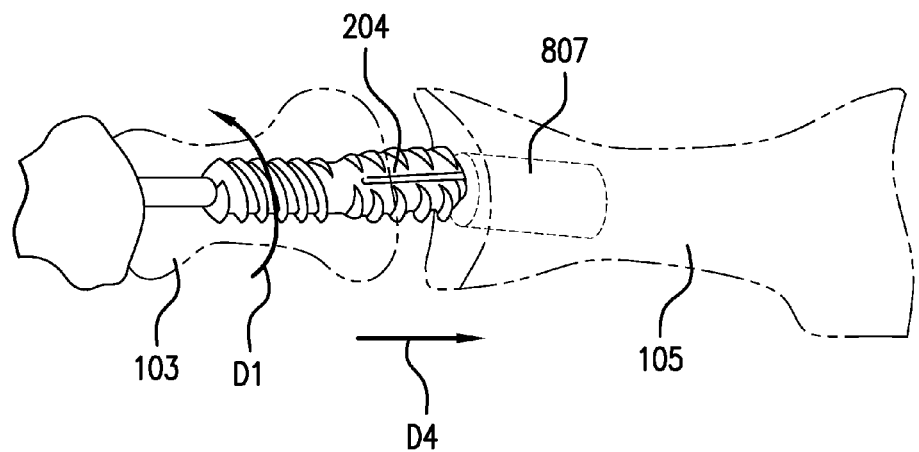
Figure 8O:
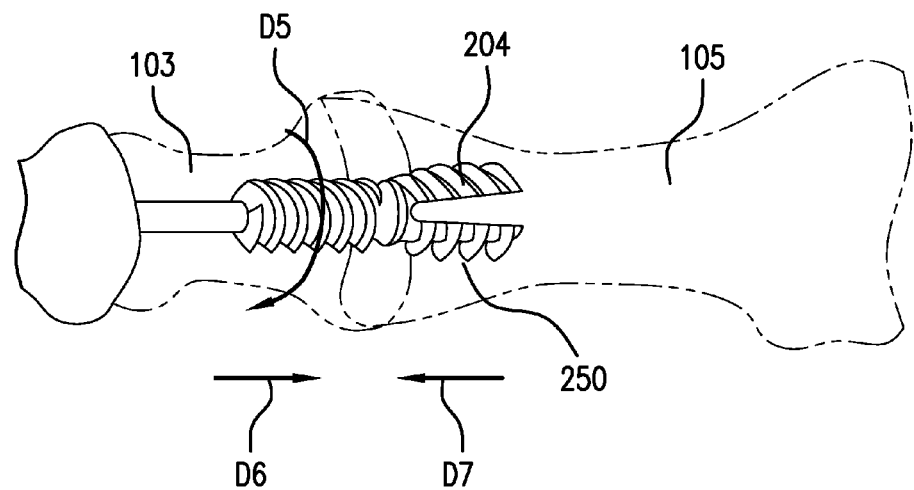
Figure 8P:
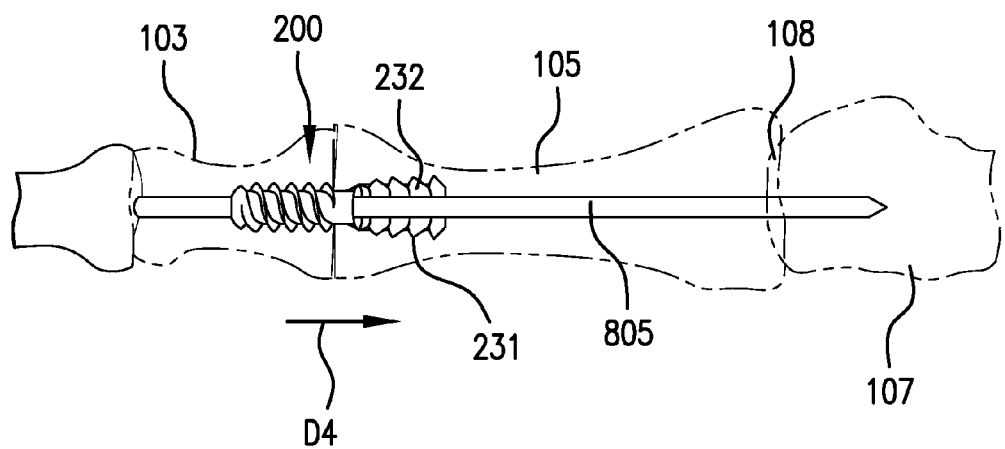

In a preferred embodiment, as shown in FIG. 8N, the middle phalanx 103 is counter-rotated in direction D1 in step 728. Preferably, the angle of rotation is in the range of about 0 degrees to about 90 degrees, more preferably about 10 degrees to about 80 degrees, and more preferably it is about 60 degrees. Next, in step 730, the second fixation portion 204 is pressed linearly into hole 807 in the proximal phalanx 105 in direction D4 lateral to the proximal phalanx 105 and hole 807. The joint is firmly compressed until the implant is completely buried and the surfaces of the resectioned joint are fully opposed as shown in FIG. 8O. Because no pressure is provided to the first and second projections 231 and 232 of second fixation portion 204 by the forceps, first and second projections 231 and 232 will deploy to substantially normal or open position as shown in FIGS. 3A-3B.

As shown in FIG. 8O, in step 732, the middle phalanx 103 is rotated to the final and desired fixation position in direction D5, thereby further advancing second fixation portion 204 into the proximal phalanx 105 via the help of the helical thread 250 formed on the second fixation portion 204. Preferably the angle of rotation is in the range of about 0 degrees to about 90 degrees, more preferably about 10 degrees to about 80 degrees, and more preferably it is about 60 degrees. The rotation in direction D5 adds further compression in directions D6 and D7 between middle phalanx 103 and proximal phalanx 105. Generally, the opposing threads of the second fixation portion 204 allow for approximately an additional 0.25 mm of compression for every 30 degree of counter-rotation. In a preferred embodiment, an angle of rotation of about 60 degrees adds about 0.5 mm compression in directions D6 and D7.

In a preferred embodiment, in step 734, as shown in FIG. 8P, the K-wire 805 is advanced in direction D4 through bore 221 in between first and second projections 231 and 232 to further deploy first and second projections 231 and 232 outwardly into an open position in the proximal phalanx 105. After the procedure, the guide wire 805 can then be removed. In an alternative embodiment, as shown in FIG. 8P, the guide wire 805 can be driven proximally into the metatarsal 107 to stabilize the metatarsophalangeal joint 108. The guide wire 805 may be left in place for the initial recovery period to allow the soft tissue to heal and prevent metatarsophalangeal joint 108 subluxation. After the initial recovery, the guide wire 805 can be removed.

As will be apparent to those skilled in the art, numerous variations may be practiced within the spirit and scope of the present invention. For example, a variety of different tools—screw drivers, wrenches, reduction instruments and drill guides—may be used in the practice of the invention. Implants of different sizes and different shapes may be used. Likewise different thread sizes and configurations may be used. There may also be variation in the procedure used to implant the intramedullary fixation implant in the bones. Certain steps can be omitted or combined with other steps and certain steps can be performed in a different order. For example, in some procedures it may not be necessary to excise the bone faces, use a K-wire, or pre-drill or pre-tap holes in the bones.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. A method for joining and compressing a first bone to a second bone of a joint, wherein the method comprising:
   providing an intramedullary fixation implant having:
      a first fixation portion; and
      a second fixation portion, wherein the second fixation portion comprises a first projection and a second projection separated by a slot, wherein the first projection and the second projection comprise a plurality of barbs shaped and arranged along the first and second projections such that they cooperatively form a thread along the second fixation portion;
   creating a first hole in the first bone;

creating a second hole in the second bone, said second hole having a longitudinal axis;

advancing the first fixation portion of the intramedullary fixation implant into the second hole in the second bone;

counter-rotating the second bone about the longitudinal axis of the second hole;

pressing the second fixation portion of the intramedullary fixation implant linearly into the first hole in the first bone; and rotating the second bone about the longitudinal axis of the second hole until the second bone is rotated into a final fixation position.

2. The method of claim 1 further comprising the step of: forming an incision over a dorsal aspect of the joint.

3. The method of claim 1, wherein the joint is selected from the group consisting of an interphalangeal joint, a metatarsal-phalangeal joint, and a metacarpophalangeal joint.

4. The method of claim 1 further comprising the step of: excising the faces of the first and second bones.

5. The method of claim 1, wherein the first fixation portion comprises threads on its exterior surface.

6. The method of claim 5, wherein the first fixation portion is advanced into the second hole in the second bone by rotatably advancing the first fixation portion via said threads into the second hole.

7. The method of claim 1, wherein the first hole is created by drilling the first hole in the first bone using a drill.

8. The method of claim 7 further comprising the step of: advancing a guide wire into the first bone for guiding the drill into the first bone.

9. The method of claim 1, wherein the second hole is created by drilling the second hole in the second bone.

10. The method of claim 1, wherein the second hole comprises threads and is created by tapping the second hole in the second bone using a tap.

11. The method of claim 10 further comprising the step of: advancing a guide wire into the second bone for guiding the tap into the second bone.

12. The method of claim 1, wherein the first projection and the second projection are flexible such that they can be collapsed from an open position to a collapsed position.

13. The method of claim 12 further comprising the step of: collapsing the first and second projections of the intramedullary fixation implant into the collapsed position before pressing the second fixation portion into the first hole in the first bone.

14. The method of claim 12, wherein the intramedullary fixation implant comprises a bore longitudinally extending through said first fixation portion and said second fixation portion.

15. The method of claim 14 further comprising the step of: advancing a guide wire through the bore of the intramedullary fixation implant to deploy the first and second projections into an open position after pressing the second fixation portion into the first hole in the first bone.

16. The method of claim 1, wherein the thread formed by the plurality of barbs along the second fixation portion translates compression between the first bone and the second bone when second bone is rotated into the final fixation position.

17. The method of claim 1, wherein the second bone is counter-rotated or rotated at an angle having a range of about 0 degrees to about 90 degrees.

18. The method of claim 1, wherein the second bone is counter-rotated or rotated at an angle having a range of about 10 degrees to about 80 degrees.

19. The method of claim 1, wherein the second bone is counter-rotated or rotated at an angle of about 60 degrees.

20. A method for joining and compressing a first bone to a second bone of a joint, wherein the method comprising:

providing an intramedullary fixation implant having:
a first fixation portion; and
a second fixation portion;

creating a first hole in the first bone;

creating a second hole in the second bone, said second hole having a longitudinal axis;

advancing the first fixation portion of the intramedullary fixation implant into the second hole in the second bone;

causing an angle of rotation between the first bone and the second bone about the longitudinal axis of the second hole;

pressing the second fixation portion of the intramedullary fixation implant linearly into the first hole in the first bone; and reversing the angle of rotation between the first bone and the second bone to a final fixation position.

* * * * *